United States Patent [19]

Wurtman et al.

[11] 4,452,815

[45] * Jun. 5, 1984

[54] METHOD OF UTILIZING D,L-FENFLURAMINE FOR MODIFYING FEEDING BEHAVIOR

[75] Inventors: Richard J. Wurtman; Judith Wurtman, both of Boston, Mass.

[73] Assignee: Massachusetts Institute of Technology, Cambridge, Mass.

[*] Notice: The portion of the term of this patent subsequent to Jan. 5, 1999 has been disclaimed.

[21] Appl. No.: 288,583

[22] Filed: Jul. 30, 1981

Related U.S. Application Data

[63] Continuation-in-part of Ser. No. 159,549, Jun. 16, 1980, Pat. No. 4,309,445.

[51] Int. Cl.³ .......................................... A61K 31/135
[52] U.S. Cl. ................................................... 424/330
[58] Field of Search ........................................ 424/330

[56] References Cited

U.S. PATENT DOCUMENTS 3,198,834  8/1965  Beregi et al. ....................... 564/375

OTHER PUBLICATIONS

Wurtman et al.–Current Medical Research & Opinion vol. 6, Supl. 1 (1979) pp. 28–33.
Wurtman et al.–Life Sciences vol. 24, (1979) pp. 895–903.
Hopkinson–Acta Psychiat. Scand. vol. 64, (1981) pp. 217–225.
Foerster et al.–Chem. Abst. vol. 91 (1979) p. 49648k.
Wurtman et al.–Chem. Abst. vol. 91 (1978) p. 99,073c.

*Primary Examiner*—Sam Rosen
*Attorney, Agent, or Firm*—Arthur A. Smith, Jr.; Paul J. Cook

[57] ABSTRACT

Compositions containing controlled amounts of d,l-fenfluramine are administered to block the intermittent carbohydrate cravings without necessarily suppressing other food intakes.

2 Claims, No Drawings

METHOD OF UTILIZING D,L-FENFLURAMINE FOR MODIFYING FEEDING BEHAVIOR

REFERENCE TO RELATED APPLICATIONS

This application is a continuation-in-part of copending application Ser. No. 159,549, filed June 16, 1980, now U.S. Pat. No. 4,309,445.

BACKGROUND OF THE INVENTION

This invention concerns a new method of treating the syndrome of carbohydrate craving during which patients present an abnormal appetite for carbohydrate at definite hours.

At the present time, patients having a strong appetite for carbohydrate were not treated before appearance of obesity. At that stage, the use of compositions of large amounts of bulky substances or appetite-suppressant drugs have been utilized. The suppression of appetite was seen to result from a propensity to eat slower, to wait longer between meals or to stop eating sooner. Such drugs show no selectivity on the kind of feeding and have unwanted side effects such as induction of hyperactivity. Obese and even normal people often describe intense cravings for high-carbohydrate foods. These cravings tend to occur at characteristic times of day and are often enhanced by stress or, in women, by premenstrual tension. The carbohydrate foods consumed to satisfy these cravings range from sweet to starchy (e.g., ice cream, crackers), and thus seem to meet a common metabolic rather than sensory need. Carbohydrate consumption enhances brain serotonin synthesis (by eliciting insulin secretion, which changes the plasma amino acid patterns to facilitate brain tryptophan uptake); thus, carbohydrate cravings might, in some people, reflect inadequate serotoninergic neurotransmission. If so, then drug treatments designed to amplify serotonin release might ameliorate this appetite disorder.

A preferred method of treatment would involve the correction of the very nature of the feeding habits of some patients having an immoderate appetite for certain kinds of carbohydrate-containing food, particularly between meals. Such a state does not always entail obesity, but can indicate some metabolic disturbances or some neurotic troubles due to anxiety of becoming overweight.

Prior to the present invention, it has been known to administer d,1-fenfluramine or fluoxetine to an animal (rat) in order to selectively reduce consumption of carbohydrates while not significantly reducing consumption of protein. These results are shown by Wurtman et al, *Science,* vol. 198, pp. 1178–1180, December, 1977; *Current Medical Research and Opinion,* vol. 6, Suppl. 1, pp. 28-33, 1979 and *Life Sciences,* vol. 24, pp. 894–904, 1979.

D-fenfluramine and d,1-fenfluramine are known anorexic agents as disclosed in U.S. Pat. No. 3,198,834. However, prior to the present invention, neither d-fenfluramine nor d,1-fenfluramine has been known to selectively reduce carbohydrate craving which occurs in patients that have an abnormal appetite for carbohydrates at definite times.

SUMMARY OF THE INVENTION

The present invention provides an appropriate treatment for carbohydrate cravings, i.e., for the patient presenting an abnormal appetite for carbohydrates at definite hours of the day or night. The invention is based on the discovery that d,1-fenfluramine selectively eliminates this abnormal and intermittent appetite for carbohydrates while maintaining a normal protein and lipid intake. The effect of d,1-fenfluramine concerns all sweet foods and those which produce glucose during the gastrointestinal transit, and that such inhibition does not function simply through a control of the caloric intake. Furthermore, this effect of d,1-fenfluramine is observed at lower dosages than that utilized for anorexic effects.

DESCRIPTION OF SPECIFIC EMBODIMENTS

The present invention relates to the administration of pharmaceutical compositions for treating the syndrome of carbohydrate craving during which the patients present an abnormal appetite at definite hours of the day or night. Specifically, the invention provides for the administration of pharmaceutical compositions having as an active ingredient the d-isomer of fenfluramine or 1-meta-trifluoro-methylphenyl-2-ethyl-aminopropane or a salt thereof mixed with an inert nontoxic pharmaceutical carrier.

Suitable additional salts can be formed from the following acids: the hydrohalic acid, sulfuric acid, phosphoric acid or an organic acid such as acetic acid, valeric acid, caproic acid, benzoic or nicotinic acid.

The inert non-toxic pharmaceutical excipient of choice utilized depends on the mode of administration. The compositions of this invention are suitable for parenteral, buccal, sublingual or rectal administration. The resulting pharmaceutical compositions are, for example, tablets, coated tablets, capsules, soft gelatine capsules, drinkable emulsions, suspensions or solutions for oral or injectable administration, sublingual tablets or suppositories. They may also be formulated into a sustained release form. Among the various excipients which may be used for these purposes include talc, magnesium stearate, calcium carbonate, sodium or magnesium phosphate, lactose or silica or the like. To the solid forms may be added a filler, a diluent, a binder such as ethyl-cellulose, dihydroxypropyl cellulose, carboxymethylcellulose, arabic gum, tragacanth gum or gelatime. The compositions of this invention may also be flavored, colored or coated with a wax or a plasticizer.

It has now been found that the d-isomer portion of d,1-fenfluramine is endowed with interesting and very specific properties which put it and its salts in a specific class among a broad disclosure of closely related compounds. This invention is based upon the discovery that the compositions of low doses of d,1-fenfluramine selectively suppress cravings for carbohydrates without disturbing the normal food intake. The use of the d-isomer for this purpose is disclosed and claimed in our co-pending application Ser. No. 159,549, filed June 16, 1980.

We have found that such a special activity of the d,1-fenfluramine, which has never been suggested, is particularly useful for the treatment of patients having at definite hours of day or night a strong carbohydrate craving that is an abnormal behavior of eating carbohydrate out of hunger.

Such patients are characterized by:
a great appetite for carbohydrate foods which are often the same,
an appetite often arising without anxiety, an appetite occurring according to a regular circadian cycle, and the resulting circadian maxima can be in relation to the menstruation cycle, often not overweight at the onset of the illness, sometimes associated with a so-called prediabetic state. These patients need at definite hours, between meals, a high level of carbohydrate consumption in the form of snacks: doughnuts, fried potatoes, potato chips, pretzels, ice cream, whole meal or chocolate cookies, etc. Such a syndrome may be linked to signs of diabetes mellitus in persons at risk.

For these patients, the administration of a composition containing between about 20 to 60 mg/day d,1-fenfluramine, depending upon the body weight of the patient, decreases the abnormal craving for carbohydrate foods at definite hours of the circadian cycle, and this result is not inhibited by the intake of a meal in which no visible alteration in the selection of basic nutrients has been observed. In accordance with this invention, d,1-fenfluramine is administered in an amount of between about 20 and 60 mg/day, preferably about 30 and 40 mg/day and most preferably by 2 or 3 equal dosages per day. At dosages above and below these amounts, the selective decrease of carbohydrate consumption does not occur to a significant degree.

The surprising and novel activity of the compositions of low doses of d,1-fenfluramine cannot be explained by the existing data on biological pharmacology of anorexic drugs which, at high doses, appear to depend on a different mechanism of action. The d-isomer of fenfluramine at usual or high dosage is more potent in inhibiting global food intake (protein and lipid as well as carbohydrate) than the 1-isomer. This activity appears to be mediated by the serotoninergic system, since:

1. The neurochemical effects of those drugs on serotonin level in the brain are significantly modified and can explain how the global food intake is inhibited.

2. Other data show that lesions of the serotoninergic terminal in specific brain areas block the effect of high doses of d,1-fenfluramine on global food intake.

3. The sedative action of these doses of d,1-fenfluramine has also been considered as a consequence of serotoninergic mechanisms.

The new properties of compositions of low doses of d,1-fenfluramine containing the d-fenfluramine which inhibit carbohydrate cravings, appear to depend on a different mechanism in relation to the central control of regulation of the energy balance: our observations show that its action is very similar to the action of somatostatin; a peptide localized in the hypothalamus, in the digestive endothelium and in the pancreatic islets. When injected into the 3rd ventricle of the rat, at very low doses, it decreases food intake and has a general behavioral effect of inhibition of the desire for carbohydrates, and inhibits absorption of carbohydrates. (Unger et al, Ann. Rev. Physiol, 1978, 40, p. 315).

While applicants do not intend to be bound by a theory of the mechanism of this invention, the following examples are merely intended to illustrate the invention and are not intended to limit the same.

EXAMPLE I

Patients, who reported a tendency to snack on high carbohydrate foods when not hungry, and who were in good health, not currently on any medication, and overweight according to standard height-weight charts, were given a physical examination and a detailed interview about their eating habits. Permission was obtained for participation in the study from subjects who passed the physical examination and who described frequent snacking on high carbohydrate food.

Two four-week studies were done (July and August, 1980). Fifteen females and two males were accepted into the first study (Table I). One subject left the study early because of a death in the family and another (X) was asked to leave due to failure to comply with the protocol; their data were not used. A third subject (Ji.La.) also left at the beginning of the fourth week; data from his first three weeks were used.

One male and eleven females were accepted into the second study (Table I). One (E.N.) left early due to sickness; her data were not used. Two others (XX and XXX) participated in the study, but their data were not used because of noncompliance with the protocol. Subjects ate all of their food in a study-designed dining area. Subjects were not allowed to work during the four weeks except for G.N.

Meals

Meals were designed to meet daily nutrient needs. In the first study, the daily caloric content was 1200 calories during the first three weeks and 950 during the final week; for the second study, meals provided 950 calories throughout. The nutrient composition of the meals corresponded to a typical American diet. In the first study, the percents of total calories from protein, carbohydrate and fat equalled 19, 46 and 32, respectively; in the second study, these were 23, 47 and 30.

Subjects had no choice of foods at mealtime. One subject in each study reported that the meals contained too many calories to permit a constant level of snacking; hence, their mealtime calories were diminished on day 3 (to 950 for F.B., study 1 and to 750 for B.C., study 2).

Caffeine-containing beverages were allowed only at mealtimes; no carbonated beverages were permitted.

A refrigerated, rented vending machine located in the dining area contained five high protein and five high carbohydrate snacks, each providing 165–179 calories (Table II). All prepared foods were carefully weighted to ensure constancy of size and caloric content.

To familiarize the subjects with the snacks prior to the start of the experiment, a buffet dinner containing all of the snacks was served on the evening before the study began.

Access to the Vending Machine

The vending machine was operated by a microcomputer, Ohio Scientific, C4PMF (Ohio Scientific, Aurora, OH). To obtain food, each subject entered a personal three-digit access code into the computer; when the code was entered, all ten windows in the vending machine unlatched. When the subject opened one window and removed the snack, the snack was replaced automatically and the other windows locked. The computer recorded which snack was chosen and the time of its removal. At the end of the study, a computer printout was made indicating the time that each snack had been taken its identity and its carbohydrate, protein and total caloric contents.

Subjects were allowed to remove as many snacks as they desired; however, they could not remove more than one during any five-minute period, share snacks or obtain them for others. The snacks had to be eaten immediately after their removal from the vending machine. No snacks could be taken from the machine at meals or thirty minutes preceding mealtimes. Although the subjects were told to keep their access code a secret, one subject in the second study (XXX) was discovered using the code of another subject (XX) to obtain food; hence, their food intake data could not be used.

Experimental Procedures

1. Maintenance of Weight

Subjects were not allowed to lose weight deliberately during the study, since it was believed that any planned reduction in caloric intake or increase in exercise would make it difficult to define the subject's normal snacking patterns or to evaluate the effects of test treatments on carbohydrate intake. To ensure compliance with this restriction on weight loss, subjects were weighed weekly. Subjects exhibiting fluctuations in weight greater than five pounds were questioned about their eating and exercise patterns. One subject (X) was asked to leave the study.

2. Treatment

Drugs and placebos were taken immediately after meals (9:30 a.m., 1:30 p.m. and 6:30 p.m.). Lactose, used as the placebo, was administered in three equally divided doses totaling 2.3 g daily. Tryptophan and d,1-fenfluramine were also administered in three equally divided doses. The total daily dose of tryptophan was 2.4 g; that of d,1-fenfluramine was 60 mg in the first study and 45 mg in the second. (The d,1-fenfluramine dose was decreased to prevent the slight drowsiness reported by a few subjects in the first study.) D,1-fenfluramine was provided by the Servier Co. (Paris, France), L-tryptophan by the Ajinomoto Co. (Todyo, Japan) and lactose by the New England Medical Center Pharmacy (Boston, MA). All were put into similarly sized white gelatin capsules to prevent subjects from identifying the substances they were receiving. All subjects took the same number of capsules.

Schedule of Drug Administration

The first two weeks of the study were used to accommodate the subjects to the new environment and eating situation, and to provide baseline data on their snacking patterns. The treatment period began on day 14 and continued through day 28. In the first study, subjects received no treatment during the first two weeks. In the second, they were given placebo capsules in order to eliminate the novelty of taking capsules. (They were not informed that the capsules contained only placebo.) All subjects in both studies were told that they would be assigned randomly to one of the three treatment groups; subjects in the second study were told that some might be receiving both placebo and a drug during the course of the experiment while others would get only placebo. Subjects were assigned to each treatment group by one of the physicians responsible for their care. The assignments were made randomly and the study was carried out double-blind. One subject, P.A., developed a skin rash after receiving d,1-fenfluramine for a week, and was switched to placebo for the second treatment week.

Data Analysis

The mean numbers of carbohydrate and of protein snacks consumed daily by each subject were determined for the baseline and treatment periods, using data from days 5–13 and 15–26 for Study 1 and days 4–13 and 15–25 for Study 2. The response of each group to its treatment was determined by comparing each subject's mean daily carbohydrate and protein snack intakes during the baseline period with those during the treatment period; paired t-test was used for this analysis. The magnitude of each subject's response to treatment was determined by comparing his or her daily snack intakes during the baseline and treatment periods; a non-paired t-test was used for this analysis because the number of baseline and treatment days sometimes differed.

For calculating the effects of a drug or placebo on snack consumption, it was anticipated that the dosages of d,1-fenfluramine or tryptophan used would most likely be short-acting, and that comparisons of the responses to post-dinner, -lunch and -breakfast doses should be made for equivalent post-treatment periods. Hence, we compared snack consumption, with and without treatment, for the dinner-midnight intervals, and omitted from consideration snacks consumed between midnight and the post-breakfast dose. These represented less than five percent of the total daily snack intake.

Days 7–10 were not included in determining Ja.Li.'s baseline snack consumption since she had a viral illness during this period; day 18 was omitted from calculations of P.A.'s treatment responses since she was switched from fenfluramine to placebo on that day.

RESULTS

Weights

Three subjects showed weight changes of greater than three pounds during the four weeks of the study: A.L. lost 12 pounds, J.L. gained 6 and D.R. gained 10 pounds. Two subjects lost 3 pounds, two gained 3 pounds, thirteen lost between 1 and 2 pounds, five gained between 1 or 2 pounds and one showed no change in weight.

Pattern of Carbohydrate and Protein Snack Consumption

The mean daily intake of carbohydrate snacks during the baseline period was $4.06 \pm 0.38$ and the mean intake of protein snacks $0.79 \pm 0.20$; these were not affected by placebo administration during this period. Thus, the subjects consumed significantly more carbohydrate than protein snacks ($P < 0.001$). Two subjects, K.N. and C.S., ate no protein snacks at all during the baseline period and fifteen ate less than one per day. The number of carbohydrate snacks consumed ranged from a low of one per day to a high of 10.5; most subjects consumed three to five per day. One subject, D.T., ate more protein snacks than carbohydrate snacks during the baseline period, when she received placebo.

Each subject's daily snack pattern was analyzed to see if the snacks tended to be consumed during particular time periods or randomly throughout the day and evening. Five time periods were considered, i.e., before breakfast (5 a.m.–9 a.m.), between breakfast and lunch (9:30 a.m.–12:30 p.m.), lunch and dinner (1:00 p.m.–5:30 p.m.), evening (6:00 p.m.–10:00 p.m.) and late evening-early morning (10:00 p.m.–5:00 a.m.). The number of carbohydrate snacks consumed during each was determined for each baseline day and expressed as the mean percent of total daily carbohydrate snack consumption (Table III). Too few subjects consistently ate protein snacks to allow a similar temporal analysis of protein snack consumption.

Four subjects tended to eat most of their carbohydrate snacks during the evening and three consumed most during the late evening. The other subjects snacked repeatedly during both the afternoon and evening. No subject consumed a major portion of snacks during the morning before breakfast.

Effect of Placebo, Tryptophan or d,1-Fenfluramine on Snack Intake

Placebo

Placebo administration to seven subjects during the treatment phase of the study had no effect on the intake of carbohydrate snacks (Table IV) for the group. As a whole, or for any individual, placebo also failed to affect protein snacking (1.12±0.58 snacks per day during the treatment period vs 0.73±0.37 protein snacks per day during the baseline period).

d,1-Fenfluramine

D,1-fenfluramine treatment significantly reduced carbohydrate snack intake in the treatment group as a whole (P<0.001) (Table VI) and in four of the subjects (Mi.Ri., D.B., and C.S.). Three of these four people ate one or more protein snacks per day during the baseline period (Mi.Ri., D.D. and B.D.); two of them (Mi.Ri. and D.D.) showed no changes in protein snacking while taking d,1-fenfluramine, while one (B.D.) decreased her protein snack intake significantly. The average number of protein snacks per day for the group was 1.17±0.27 during pretreatment and 0.71±0.26 when receiving d,1-fenfluramine.

Tryptophan

Three subjects showed a significant decrease in carbohydrate snack intake after tryptophan administration (Ma.Ri., L.H. and K.N.). Ma.Ri.'s carbohydrate snack intake ranged from one to four snacks per day on tryptophan. His protein intake also diminished slightly, from a baseline range of zero to three snacks per day to a treatment range of zero to two snacks per day; however, he consumed protein snacks consistently during both control and treatment periods. L.H. ate four to eleven carbohydrate snacks per day while on placebo, and four to six while on tryptophan; her range of protein snacks on placebo was zero to three snacks, and on tryptophan, zero to two. K.M.N. ate two to seven carbohydrate snacks per day during the baseline period, and one to five per day on tryptophan; on 11 of the 13 test days, she ate only one or two carbohydrate snacks per day. (K.M.N. did not eat any protein snacks during the baseline or treatment periods.)

One other subject, D.C., showed a consistent but not significant reduction in carbohydrate snack consumption, from one to four per day during the baseline period, to zero to two while on tryptophan. G.H. significantly increased her carbohydrate intake during the tryptophan treatment period.

Although tryptophan did not produce a significant reduction in the consumption of carbohydrate snacks by the group as a whole, it did have a significant effect in three of the eight subjects (Table V). Protein snack consumption for the group as a whole was 1.1±0.27 snacks per day during the pretreatment period and 0.95±0.28 during the treatment period.

The Effect of Tryptophan and d,1-Fenfluramine on the Time of Carbohydrate Snack Consumption If carbohydrate snacking reflects a specific neurochemical need that is ameliorated by the metabolic effects of carbohydrate consumption and if a nonspecific anorectic drug is given before peak carbohydrate desire fails to provide this neurochemical change, then it might be anticipated that when the anorexia wore off, the carbohydrate craving would reoccur. Thus, if in this study, d,1-fenfluramine or tryptophan acted as general anorectic drugs, it would have been expected to see evidence of carbohydrate craving after the anorexia they produced had ended. Such a delay was not observed: d,1-fenfluramine treatment delayed the peak time of carbohydrate snacking in only one of the responders and this change (as reflected by the time of day in which 50 percent of the carbohydrate snacks were eaten) involved only 15–30 minutes. None of the three subjects who responded to tryptophan by decreasing carbohydrate snack intake (K.M., Ma.Ri. and L.H.) changed their times of peak carbohydrate snacking. These observations suggest that the suppression of carbohydrate snacking observed in some subjects after administration of d,1-fenfluramine and tryptophan reflected not a nonspecific inhibition of desire for all foods, but a specific suppression of carbohydrate appetite—as might occur after carbohydrate consumption.

This study provides evidence that overweight people who claim to have a craving for carbohydrate-rich foods actually do elect to consume large amounts of such foods when given a choice between carbohydrate and protein-rich snacks. Moreover, the time of day when carbohydrate snacking is most likely to occur tends to be characteristic for each individual. D,1-fenfluramine reduced significantly the number of carbohydrate snacks consumed in the treatment group as a whole and in four of nine subjects; tryptophan significantly decreased carbohydrate snack consumption in three of eight subjects, but not in the treatment group as a whole. Protein snack consumption was not consistently affected by either of these treatments among the subjects who routinely ate some protein snacks.

Because d,1-fenfluramine is an anorectic agent, its administration may have dimished carbohydrate snacking by reducing hunger in general. Moreover, the three daily meals supplied about 50 percent fewer calories than the subjects ate prior to the study, suggesting that their snacking may have been motivated by hunger as well as by a particular desire to eat carbohydrates. If this were so, and if fenfluramine suppressed carbohydrate snacking by making the subjects less hungry, then the effect of the drug should have been most pronounced at times of day when subjects were most likely to be hungry. Since the subjects had access to the vending machine snacks at all times except at mealtimes, their hunger should have been most intense at times when they were not snacking nor had recently eaten many calories at meals. Such a period was the morning (9:30 a.m.–12:30 p.m.) since breakfast both provided 50 percent fewer calories than dinner and was not preceded by snacking (even though many subjects were awake for at least an hour before it was served). Conversely, subjects should have been least hungry after dinner since that meal contained the most calories, and followed many hours of potential snack intake. The temporal pattern of snacking exhibited by the subjects during the baseline weeks did not reflect this expectation: the subjects ate snacks least frequently during the morning hours and most frequently during the afternoon and evening, or during the evening alone (Table III). Thus, it seems unlikely that the subjects snacked simply because they felt calorically deprived and generally hungry. (They also failed to complain of hunger.) D,1-fenfluramine did not change the number of snacks consumed during the morning, when the subjects might have been most hungry; its greatest effect was seen during the afternoon and evening. Since these were periods when the subjects were least likely to be hungry, it is also doubtful that d,1-fenfluramine treatment diminished carbohydrate snacking by a nonspecific anorectic effect.

The doses of d,1-fenfluramine used in this study (60 mg daily, Study 1 and 45 mg daily, Study 2) are below those generally used clinically to produce anorexia. The number of snacks consumed from midnight to the next morning was analyzed since this period coincided with the termination of d,1-fenfluramine's effect. Snacking during this period was similar during the baseline and treatment periods, suggesting the lack of rebound eating after the drug wore off.

The protocol used in this study allowed obese subjects to consume carbohydrate or protein snacks whenever they wished, and allowed the investigators to assess the value of specific drugs on the consumption of specific macronutrients (protein and carbohydrate). The rejection of the protein snacks and frequent consumption of carbohydrate snacks by the subjects indicates that some obese people do not simply overeat any food, but select particular foods to satisfy particular appetites. This finding suggests that the treatment of obesity should include evaluation of the patient's food intake patterns before beginning diet therapy, and determination of whether he or she consumes food in excess or only certain macronutrients. Moreover, the time during which the subject is most likely to overeat certain types of foods should be known in order to develop diet plans that allow the dieter to satisfy his craving for particular foods when he is most likely to want them. If the dieter cannot control intake of specific foods like carbohydrate-rich snacks, anorectic drugs that decrease cravings for these foods could be incorporated into the treatment. Since the desire for such foods is not distributed equally over the entire day, the drugs can be reserved for administration before the period when consumption of the snacks is most likely to occur. This method of treatment may slow the development of drug tolerance and may also better treat the patient's specific appetite disturbance.

TABLE 1

Profile of subjects*

| Subject | Age | Ht | Wt | Sex | % High-CHO snacks* | Onset test period | Test snack food |
|---|---|---|---|---|---|---|---|
| A.P. | 31 | 5'5" | 116 | f | 60 | 3 pm | cookies |
| R.F. | 25 | 5'9" | 150 | m | 72 | 3 pm | cookies |
| J.T. | 34 | 5'5" | 223 | f | 60 | 3 pm | cookies |
| S.H. | 24 | 5'3" | 110 | f | 73 | 8 am | candy |
| R.S. | 58 | 5'3" | 190 | f | 61 | 2 pm | crackers |
| A.C. | 50 | 5'6" | 160 | f | 72 | 4 pm | cookies |
| D.S. | 30 | 5'7" | 140 | f | 60 | 10 am | cake |
| M.F. | 28 | 5'7" | 150 | f | 91 | 10 am | crackers |
| J.A. | 63 | 5'5" | 135 | m | 100 | 3 pm | cookies |
| C.W. | 20 | 5'5" | 98 | f | 60 | 8 pm | cookies |
| K.J. | 30 | 5'10" | 170 | f | 95 | 7:30 pm | cookies |

*Subjects were asked to keep an 8-day record of food intake. The number of snacks consumed per day during the 8-day period was determined and the percent of snacks consisting of high-carbohydrate and high-protein foods characterized (see Methods). Drug administration was timed to occur 1 h prior to the time of day when, for each subject, most frequent snacking occurred. The test snack food for each subject was chosen in consultation with the subject. All subjects continued to live at home and maintain their normal schedule during the study.

TABLE II

VENDING MACHINE SNACK FOODS

| Food | Calories | Protein (g) | CHO (g) |
|---|---|---|---|
| Ham and cheese | 165 | 15 | 0 |
| Potato chips | 160 | 1 | 14 |
| ½ Bagel and creamcheese | 160 | 4 | 21 |
| Meatballs | 179 | 16 | 4* |
| Chocolate chip cookies | 175 | 1 | 20 |
| Salami and cheese | 160 | 0 | 20 |
| M & M candies | 175 | 0 | 21 |
| Barbecued pork chops | 160 | 16 | 4** |
| Chocolate cupcake[1] | 160 | 2 | 25 |
| ½ Cranberry muffin[2] and butter | 175 | 3 | 20 |
| 3 Cocktail frankfurters | 165 | 7 | 1 |

Foods are listed in the same vertical order as their placement in the vending machine.
*CHO is from catsup and breadcrumbs in meatball mixture.
**CHO is from barbecue sauce.
[1]Used in Study 1.
[2]Used in Study 2.

TABLE 3

Effect of 1-tryptophan or d1-fenfluramine on consumption of carbohydrate-rich snack foods*

| | CHO consumed (g) | | | |
|---|---|---|---|---|
| Subject | Tryptophan Placebo | Tryptophan (2 g) | Fenfluramine Placebo | Fenfluramine (20 mg) |
| J.A. | 20 | 14 | 22 | 20 |
| M.F. | 16 | 14 | 19 | 13 |
| A.P. | 18 | 30 | 18 | 4 |
| R.S. | 34 | 21 | 29 | 0 |
| J.T. | 43 | 48 | 66 | 46 |
| K.J. | 66 | 28 | 40 | 8 |
| C.W. | 43 | 32 | 26 | 14 |
| S.H. | 9 | 4 | 5 | 7 |
| A.C. | 27 | 41 | 20 | 24 |
| D.S. | 44 | 67 | 22 | 39 |
| R.F. | 83 | 101 | 200 | 162 |

*Data are expressed as mean snack-food carbohydrate consumed per day during the 4-h test period. Subjects took fenfluramine, tryptophan or their placebos 1 h prior to the onset of a predetermined carbohydrate snacking period. Carbohydrate snacks were restricted to a specific premeasured item for each subject (Table 1). Most subjects consumed other foods during the 4-h period. This table represents the carbohydrate consumed from the snack item.

TABLE IV

EFFECT OF PLACEBO ON CONSUMPTION OF CARBOHYDRATE SNACKS

| | Carbohydrate Snacks per Day | |
|---|---|---|
| Subjects | Control | Placebo |
| A.L. | 3.0 ± .31 | 2.7 ± .39 |
| F.B. | 1.6 ± .33 | 1.4 ± .42 |
| E.N. | 3.2 ± .43 | 4.0 ± .28 |
| J.R. | 5.3 ± .27 | 7.4 ± .42 |
| G.N. | 3.0 ± .56 | 2.7 ± .47 |
| D.T. | 2.7 ± .57 | 2.7 ± .48 |
| B.C. | 2.3 ± .39 | 1.8 ± .18 |

Subjects A.K., F.B., E.N and J.R. (first study) received no treatment for the first two weeks and placebo (lactose 2.3 g per day in 3 divided doses) during the second two weeks. Subjects G.N., D.T. and B.C. (second study) received placebo during both the first and second two-week periods. In all cases subjects did not know whether pills given during either period would be placebo or treatment. Comparisons for each subject were made between mean snack intakes during days 4 or 5 through 13 and 15 through 25 or 26, respectively.
Data are expressed as means ± S.E.M.

TABLE V

EFFECT OF TRYPTOPHAN ON CONSUMPTION OF CARBOHYDRATE SNACKS

| | Carbohydrate Snacks per Day | |
|---|---|---|
| Subjects | Control | Tryptophan |
| D.K. | 10.5 ± 1.10 | 13.0 ± .63 (n.s) |
| G.H. | 4.7 ± .63 | 7.5 ± .67 (P < 0.01)* |
| K.M. | 4.0 ± .53 | 2.2 ± .35 (P < 0.02) |

TABLE V-continued
EFFECT OF TRYPTOPHAN ON CONSUMPTION OF CARBOHYDRATE SNACKS

| | Carbohydrate Snacks per Day | |
|---|---|---|
| Subjects | Control | Tryptophan |
| D.C. | 2.4 ± .43 | 1.3 ± .22 (n.s.) |
| M.B. | 3.1 ± 1.10 | 3.6 ± 1.00 (n.s.) |
| Ma.Ri. | 4.4 ± .33 | 2.6 ± .29 (P < 0.001) |
| P.R. | 4.0 ± .31 | 3.6 ± .28 |
| L.H. | 6.6 ± .36 | 4.7 ± .34 (P < 0.05) |

Subjects D.J., G.H., K.M., D.C. and M.B. (first study) received no treatment for the first two weeks and tryptophan (2.4 g per day in three divided doses) during the second two weeks. Subjects Ma.Ri., P.R. and L.H. (second study) received placebo during the first two-week period and tryptophan during the second two weeks (213 g per day in three divided doses). Comparisons for eacDh subject were made between mean snack intakes during days 4 or 5 through 13, and 15 through 25 or 26 respectively.

Data are expressed as means ± S.E.M.

*Increased from control.

TABLE VI
EFFECT OF FENFLURAMINE ON CONSUMPTION OF CARBOHYDRATE SNACKS

| | Carbohydrate Snacks per Day | |
|---|---|---|
| Subjects | Control | Fenfluramine |
| K.L. | 7.7 ± .42 | 5.7 ± .37 (n.s.) |
| D.B. | 1.0 ± .02 | 0.1 ± .08 (P < 0.001) |
| P.A. | 2.3 ± .33 | 1.8 ± .40 (n.s.) |
| B.D. | 4.7 ± .53 | 1.1 ± .21 (P < 0.001) |
| Ja.La. | 4.6 ± .90 | 2.3 ± .47 (n.s.) |
| C.S. | 2.7 ± .27 | 0.8 ± .21 (P < 0.001) |
| Mi.Ri. | 4.7 ± .42 | 3.1 ± .32 (P < 0.001) |
| Ja.Li. | 5.1 ± .70 | 3.5 ± .43 (P < 0.05) |
| D.D. | 5.1 ± .63 | 3.0 ± .66 (P < 0.05) |

Subjects K.L., D.B., P.A., B.D.. Ja.La. and C.S. (first study) received no treatment for the first two-week period and fenfluramine (60 mg per day in three divided doses) during the second two weeks. P.A. received fenfluramine for six days and was then switched to placebo for seven days; during this period she consumed 2.8 ± .54 carbohydrate snacks per day. Subjects Mi.Ri., Ja.Li. and D.D. (second group) received placebo for the first two weeks and fenfluramine (45 mg per day in three divided doses) for the second two weeks. Comparisons for each subject (except for P.A.) were made between mean snack intake during days 4 or 5 and 15 through 25 or 26, respectively.

Data are expressed as means ± S.E.M.

We claim:
1. A method of treating human patients having the syndrome of abnormal carbohydrate craving, between meals which consists of administering to said patient between about 20 and 60 mg/day of d,1-fenfluramine.
2. A method of claim 1 wherein the dosage of the d,1-fenfluramine ranges from 30 to 50 mg/day.

* * * * *